United States Patent [19]
Matsui et al.

[11] Patent Number: 6,160,615
[45] Date of Patent: Dec. 12, 2000

[54] SURFACE MEASUREMENT APPARATUS FOR DETECTING CRYSTAL DEFECTS OF WAFER

[75] Inventors: Shigeru Matsui, Hitachinaka; Muneo Maeshima, Mito; Isao Nemoto, Hitachinaka, all of Japan

[73] Assignee: Hitachi, Ltd., Tokyo, Japan

[21] Appl. No.: 09/255,766

[22] Filed: Feb. 23, 1999

[30] Foreign Application Priority Data

Feb. 24, 1998 [JP] Japan .................................. 10-042089

[51] Int. Cl.[7] ........................... G01N 21/00; G01B 11/06; C23C 16/00
[52] U.S. Cl. .................... 356/237.4; 356/237.5; 356/381; 356/382; 427/248.1
[58] Field of Search .................. 324/765, 768, 324/769, 533, 534, 501; 356/237.4, 237.5; 427/248.1

[56] References Cited

U.S. PATENT DOCUMENTS 5,432,607 7/1995 Taubenblatt ..................... 356/237.5
5,903,342 5/1999 Yatsugake et al. ................. 356/237.4
5,925,411 7/1999 Van De Van et al. .............. 427/248.1

FOREIGN PATENT DOCUMENTS 7249559 9/1995 Japan .
888265 4/1996 Japan .

*Primary Examiner*—Frank G. Font
*Assistant Examiner*—Armando Rodriguez
*Attorney, Agent, or Firm*—Kenyon & Kenyon

[57] ABSTRACT

A sample is supported flat in high precision by a sample chuck, and is easily mounted and dismounted.

A wafer lifting mechanism is arranged in a position separated from a rotating system of a rotatable wafer chuck, and a wafer is lifted from a supporting surface by moving the wafer lifting mechanism upward to let pins penetrate through through holes of the wafer chuck under a state that the wafer chuck is stopped at a sample mounting-and-dismounting position.

9 Claims, 4 Drawing Sheets

SURFACE MEASUREMENT APPARATUS FOR DETECTING CRYSTAL DEFECTS OF WAFER

BACKGROUND OF THE INVENTION

The present invention relates to a surface measurement apparatus suitable for evaluating crystal defects of a semiconductor wafer and detecting extraneous particles attached on a surface of the semiconductor wafer, and particularly to a surface measurement apparatus suitable for measuring a surface state of a sample (wafer) with a high precision.

With increase in the degree of integration of an LSI (large-scale integration) circuit, there arises a serious problem in that the yield of conforming items and the reliability of MOS (metal oxide semiconductor) transistors composing the LSI circuit are decreased due to failures in the transistors. As a cause of the MOS transistor failures, typical problems are dielectric breakdown in a gate oxide film and an excessive leakage current in a junction. Most of the MOS transistor failures are caused directly or indirectly by crystal defects in a silicon substrate. That is, when a crystal defect exists in a surface area of the silicon substrate to be converted to a silicon oxide film by oxidization in an LSI circuit manufacturing process, a structural defect is formed in the silicon film to cause dielectric breakdown when the LSI circuit is operated.

Further, when a crystal defect exists in a depletion layer of a junction, the leakage current becomes larger. As described above, it is not preferable that a crystal defect is formed in a surface area in a silicon wafer where an element is to be formed because a MOS transistor failure will be caused.

Therefore, defect measurement of a silicone substrate is important in the quality control of silicon crystal.

In regard to the method of measuring such a defect, there is a technology described in a paper by Takeda in "Applied Physics", Vol. 65, No. 11 (1996), page 1162. In the method, two light beams having wavelengths of which penetration depths to a solid are different from each other by three times or more are irradiated from oblique incident light irradiating optical systems onto a wafer surface, and the intensity of the scattered light from a crystal defect is detected from a direction normal to the wafer surface. In the measuring method employing such an oblique incident light irradiating optical system, when the irradiating beam size is finely focused and the wafer adhered onto a wafer chuck is warped, the position irradiated by the beam is vertically changed according to change in the position of the wafer surface. The position irradiated by the oblique incident beam is moved on the sample surface in a direction parallel to the sample surface due to the vertical change. Supposing the irradiating beam is irradiated at the Brewster angle (75°) of silicon and the height of the wafer surface is changed by 0.5 micrometers due to the reason described above, the position irradiated by the beam is changed on the wafer surface by approximately 1.9 micrometers. At the same time, the intensity of the scattered light cannot be accurately measured because the detecting position of the detection system is vertically changed due to the vertical change of the wafer surface. Therefore, it is necessary to maintain the relative position between the irradiated area and the detecting system area constant and to maintain the distance between them and the sample surface.

Therefore, it is necessary that a wafer chick having a highly flat mounting surface is used and a wafer is forcibly laid along the mounting surface of the wafer chuck by adhering the back surface of the wafer to the mounting surface using a vacuum force or an electrostatic force to adjust flatness of the wafer surface so as to become flat even if the wafer is warped.

However, in the supporting method of adjusting flatness of the wafer surface so as to become flat by adhering the back surface of the wafer to the mounting surface of the wafer chuck using a vacuum force or an electrostatic force, when a gap between the outer peripheral edge of the wafer and the mounting surface of the wafer chuck is formed, the outer peripheral edge portion of the wafer is bent in that portion and accordingly the gap cannot be formed. Therefore, it becomes difficult to insert a pair of tweezers for detaching the wafer or a transfer hand for automatically transfer the wafer between the wafer and the wafer chuck. Particularly, this problem becomes clearer in a case of employing a wafer chuck usable to plural kinds of wafers having different diameters. This is because when a wafer having a diameter smaller than a maximum diameter which the wafer chuck can handle is mounted on the wafer chuck, the mounting area of the wafer chuck becomes larger than the diameter of the mounted wafer.

Therefore, when the wafer is detached from the wafer chuck, a wafer lifting mechanism for lifting off the wafer from the wafer chuck is required.

In order to perform measurement over the whole surface of a wafer by scanning a finely focused spot of irradiating light over the wafer surface, a crystal defect measurement apparatus is designed so that the wafer is linearly moved in the radial direction while being rotated using a stage having shafts movable in the radial direction and the rotating direction of the wafer. Therefore, the wafer lifting mechanism used in such a crystal defect measurement apparatus is on the premise that it is combined with a rotating stage.

As an example of the conventional wafer lifting mechanism, a technology used in a rotating stage is disclosed in Japanese Patent Application Laid-Open No.7-249559. The mechanism comprises a rotatable stage which adheres and supports only the central portion of a wafer, and a transfer hand having U-shaped top ends or a transfer hand adhering the wafer at the peripheral portion off the central portion of the wafer is combined with a vertical moving mechanism to lift the wafer off from the wafer chuck of the rotating stage.

As another example of the conventional wafer lifting mechanism, a technology used in a positing stage of an exposure apparatus is disclosed in Japanese Patent Application Laid-Open No.8-88265. The mechanism comprises an XY stage movable in two axial directions intersecting each other at right angle, and the wafer lifting mechanism is mounted on the XY stage mechanism. When a wafer is moved along these shafts, the wafer lifting mechanism is moved together with the wafer chuck.

The conventional wafer lifting mechanism used in such a rotating stage is very difficult to insert the transfer hand into the back surface of the wafer in a case of using the wafer chuck adhering the almost whole outer peripheral edge of the back surface of the wafer such as in the crystal defect measurement apparatus, and particularly in a case where the diameter of the mounting surface of the wafer chuck is larger than the diameter of the wafer to be adhered and mounted.

Further, in a case of employing the rotating stage, the wafer lifting mechanism is difficult to be integrally constructed with the chuck rotating mechanism because the volume and the weight of the rotating portion must be reduced, because the rotating unbalance in respect to the rotating shaft must be decreased, and because in an rotating stage using a power source such as electricity or pressurized gas, the wiring or the piping is installed in the inside of the rotating shaft so that the rotating shaft may be rotated.

SUMMARY OF THE INVENTION

In order to solve the technical problems in the conventional apparatus, an object of the present invention is to provide a surface measurement apparatus which can highly precisely measure a surface of a sample by rotating the sample while being supported on a supporting surface of a sample chuck in a flat state at high precision and can easily mount and dismount the sample onto and from the supporting surface of the sample chuck.

Another object of the present invention is to provide a surface measurement apparatus which is suitable for detecting a crystal defect of a wafer and an extraneous particle attached on the surface of the wafer.

In detail, if a retreated portion (for example, a depression) for inserting a transfer handle or a pair of tweezers is formed at a position in the supporting surface for adhering and supporting a sample (for example, a silicon wafer) corresponding to the whole or a part of the outer peripheral edge of the sample, the outer peripheral edge opposite to the retreated portion becomes a free end to cause bend at that portion. Therefore, the object of the present invention is to provide a surface measurement apparatus which is designed so as to easily transfer the sample between the sample chuck and the transfer hand or the pair of tweezers without forming such a retreated portion in the supporting surface.

The surface measurement apparatus in accordance with the present invention is suitable for detecting an extraneous particle attached on a sample such as a silicon wafer or for detecting a crystal defect in an inside near the surface of the sample based on reflected light which is formed by irradiating light onto the surface of the sample supported on the supporting surface of the sample chuck.

A feature of the present invention is a surface measurement apparatus comprising a sample chuck for supporting a sample by adhering a back surface of the sample to a supporting surface; a rotating mechanism for rotating the sample chuck; a base member for supporting the rotating mechanism; a sample lifting mechanism for lifting the sample on the supporting surface of the sample chuck off from the supporting surface; and an optical measurement system for measuring the surface of the sample supported to the sample chuck to be rotated, wherein the supporting surface of the chuck comprises a flat surface for the substantially whole periphery of an outer peripheral edge of the sample to be supported; and a through hole for letting the sample lifting mechanism pass through, the through hole being formed in the flat surface, and the sample lifting mechanism is arranged in the side of the base member, the sample lifting mechanism being extended so as to lift the sample off from the supporting surface by penetrating said through hole when the sample chuck is stopped at a predetermined position.

Another feature of the present invention is a surface measurement apparatus comprising a sample chuck for supporting a sample by adhering a back surface of the sample to a supporting surface; a rotating mechanism for rotating the sample chuck; a first base member for supporting the rotating mechanism; a second base member for linearly movably supporting the first base member; a sample lifting mechanism for lifting the sample on the supporting surface of the sample chuck off from the supporting surface; and an optical measurement system for measuring the surface of the sample supported to the sample chuck to be rotated, wherein the supporting surface of the chuck comprises a flat surface for the substantially whole periphery of an outer peripheral edge of the sample to be supported; and a through hole for letting the sample lifting mechanism pass through, the through hole being formed in the flat surface, and the sample lifting mechanism is arranged in the side of the second base member, the sample lifting mechanism being extended so as to lift the sample off from the supporting surface by penetrating the through hole when the sample chuck is stopped at a predetermined position.

As the other features of the present invention, number of the through holes described above is plural, and each of the through holes is formed at a position keeping away from a position opposite to the outer peripheral edge of the sample to be mounted on and adhered to the supporting surface.

Further, the sample lifting mechanism comprises a plurality of cylindrical pins vertically moved through the through hole, each of the cylindrical pin having a sucking opening for vacuum adhering at a top end of the cylindrical pin so as to vacuum adhere the back surface of the sample, the plurality of pins being coupled with each other by a coupling member to be vertically moved at a time by a single vertical drive mechanism. An air cylinder is employed in the vertical drive mechanism.

Further, the sample chuck comprises a vacuum adhering system for vacuum adhering the sample onto the supporting surface, and the vacuum adhering system is released to atmospheric pressure and the cylindrical pin of the sample lifting mechanism is moved upward through the through hole while the sucking opening in the top end of the cylindrical pin is being evacuated when the sample supported on the support surface is lifted up from the supporting surface.

The optical measurement system comprises a light irradiating optical system for irradiating a light beam composed of two wavelengths of which penetration depth to the sample is different from each other by three times or more; and a light receiving optical system for converting an intensity of scattered light into an electric signal, the scattered light being scattered to a direction normal or oblique to the sample surface.

DESCRIPTION OF THE PREFERRED EMBODIMENTS

Figure 1:
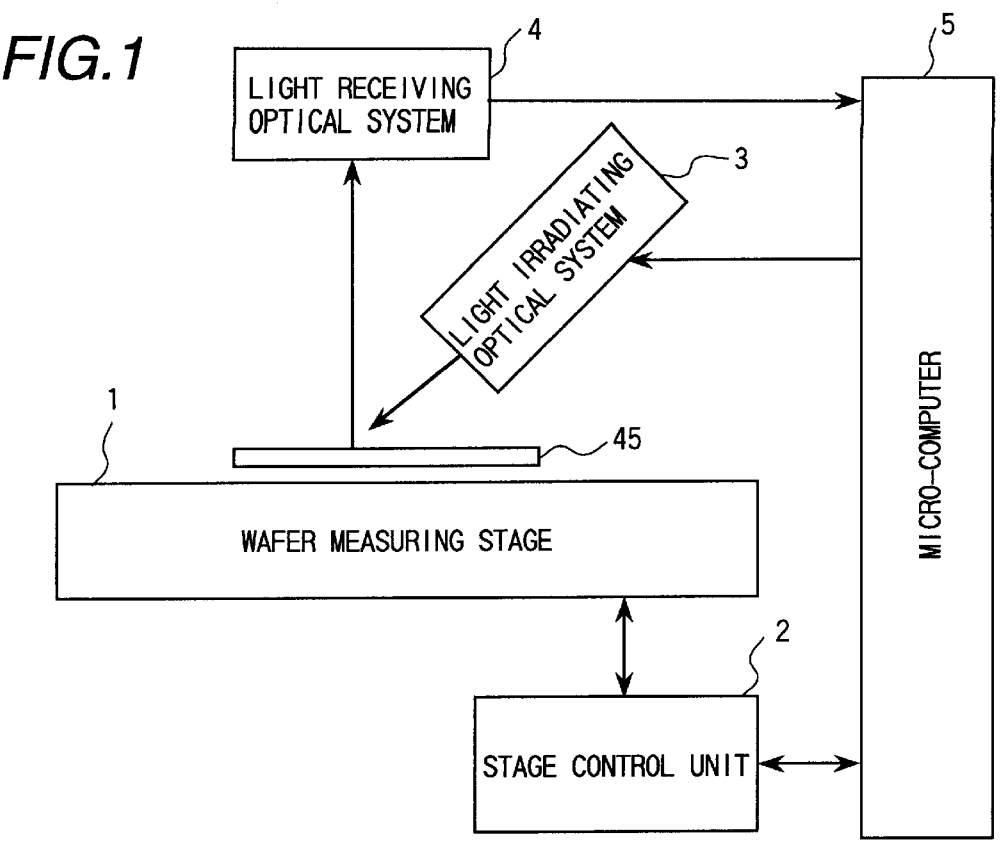
FIG. 1 is a block diagram showing a wafer crystal defect measurement apparatus in accordance with the present invention.

FIG. 1 is a block diagram showing the construction of a wafer crystal defect measurement apparatus in accordance with the present invention. In the illustrated apparatus, a silicon wafer is used as a sample, and a crystal defect in the inside near of the surface of the silicon wafer is detected by measuring the surface. The wafer crystal defect detecting apparatus comprises a wafer measuring stage 1 for mounting a silicon wafer 45 to be performed with defect detection and for rotating and linearly moving the silicon wafer; a stage control unit 2 for controlling operation of the wafer measuring stage 1; a light irradiating optical system 3 for irradiating light from a laser of light source onto the surface of the silicon wafer 45; a light receiving optical system 4 for receiving reflected light which the laser light beam irradiated onto the surface of the silicon wafer 45 generates by being scattered by a crystal defect inside the silicon wafer 45 or an extraneous particle attached onto the surface and for converting the received light into an electric signal; and a microcomputer 5 for instructing operation of the whole apparatus and collecting measured data, for performing measuring and detecting processing, and for performing control processing such as displaying and recording of the results.

Figure 2:
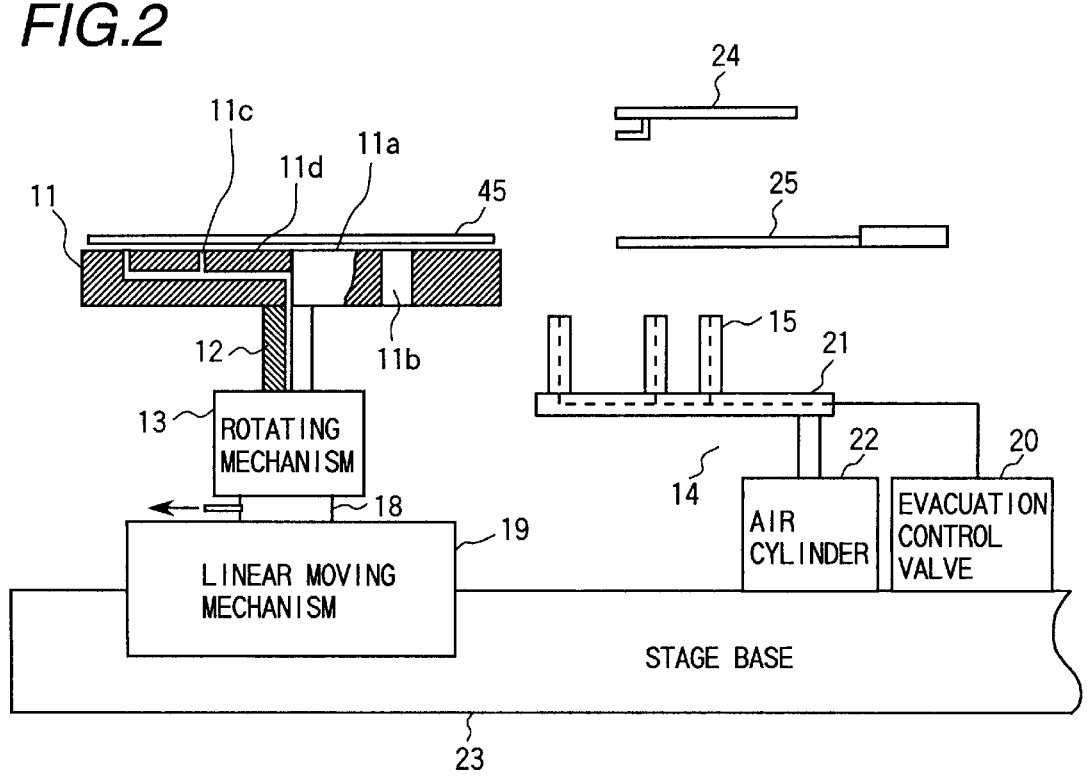
FIG. 2 is a side view showing a wafer measurement stage in the wafer crystal defect measurement apparatus shown in FIG. 1.
Figure 3:
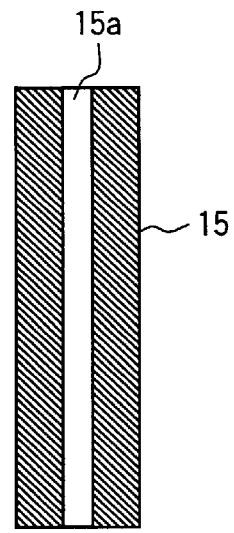
FIG. 3 is a vertical cross-sectional side view showing a pine in the wafer measurement stage shown in FIG. 2.

FIG. 2 is a side view showing the construction of the wafer measurement stage 1 described above in detail.

A wafer chuck 11 as a sample chuck having a supporting surface 11a for supporting the silicon wafer 45 in a flat state by vacuum adhering is constructed so as to be rotated together with a rotating shaft 12, and can be continuously rotated by a rotation mechanism 13.

The supporting surface 11a of the wafer chuck 11 is formed in such a flat surface that the silicon wafer 45 may be supported in a flat state by closely vacuum adhering the nearly total surface of the back surface of the silicon wafer 45 except for portions of through holes 11b through which pins 15 of a wafer lifting mechanism 14 are vertically moved and portions of sucking openings 11c for vacuum adhering. If there exist a wide-width depressed portion at a position on the supporting surface 11a opposite to the outer peripheral edge of the silicon wafer 45 to be adhered and supported, the portion of the outer peripheral edge of the silicon wafer 45 becomes a free open edge to be easily bent. Therefore, it is avoided to form such a depressed portion.

A vacuum adhering evacuation passage 11d connected to the sucking openings 11c is formed inside the wafer chuck 11. The vacuum adhering evacuation passage 11d is connected to a vacuum pump, not shown, through the inside of the rotating shaft 12 and further through a connector 18 relatively rotatably connected to the rotating shaft 12.

By such a construction, the wafer chuck 11 can be rotated in a state that the silicon wafer 45 is supported in a flat state by vacuum adhering the back surface of the silicon wafer 45.

The rotating mechanism 13 is composed of a rotary motor for generating a rotating force, a rotary encoder for generating rotation angle information and a control circuit for these components. A stationary member side of the rotating mechanism 13 is arranged on a linear moving mechanism 19 which is reciprocally and horizontally moved on a sage base 23 of this apparatus.

The linear moving mechanism 19 comprises a propelled force generating means formed by combining a linear motor or a rotary motor and a ball screw, a linear scale (linear encoder) for generating moving position information and a control circuit for these components.

The wafer lifting mechanism 14 comprises three pins 15 having sucking openings 15a for vacuum sucking the wafer back surface in the upper end portion of the wafer lifting mechanism, a coupling member 21 for coupling the three pins 15, an air cylinder 22 with a linear scale for vertically driving the coupling member 21 with a compressed air force, an evacuation control valve 20 for controlling vacuum evacuation of the sucking openings 15a, and a control circuit for these components. A stationary member of the air cylinder 22 and the evacuation control valve 20 are arranged in the side of the stage base 23 which supports a movable portion of the linear moving mechanism 19.

The wafer lifting mechanism 14 is arranged at a wafer mounting-and-dismounting position for mounting and dismounting the wafer 45 onto and from the wafer chuck 11 by cooperating with a pair of wafer tweezers 24 and a transfer hand 25, and the silicon wafer 45 is mounted or dismounted onto or from the supporting surface 11a by vertically moving the pins 15 when the wafer chuck 11 is moved to the wafer mounting-and-dismounting position and rotated to a mounting-and-dismounting angle using the rotating mechanism 13 and the linear moving mechanism 19 controlled by the stage control unit 2.

Description will be made below on the operating procedure of mounting and dismounting the silicon wafer 45 onto and from the wafer chuck 11 of the wafer measurement stage 1 in the present embodiment.

Control of the operation is performed by the stage control unit 2 based on instruction from the microcomputer 5. In regard to the rotating mechanism 13, a rotating speed and a stopping angle of the rotary motor are controlled by receiving rotating angle information of the rotating shaft 12 (the wafer chuck 11) from the rotary encoder. In regard to the linear moving mechanism 19, a horizontal moving speed and a stopping position of the linear motor are controlled by receiving horizontal position information from the linear scale. In regard to the wafer lifting mechanism 14, an expanding amount of the air cylinder 22 and the evacuation control valve 20 are controlled by receiving vertical position information of the air cylinder 22 (the top end of the pin 15) from the linear scale.

Initially, description will be made below on the procedure of mounting the silicon wafer 45 onto the wafer chuck 11. When the linear moving mechanism 19 is at a preset wafer mounting-and-dismounting position and the rotating mechanism 13 is at a preset wafer mounting-and-dismounting angle, the wafer 45 can be transferred to the wafer chuck 11 through the following procedure because the wafer chuck 11 is positioned at such a relative position that the three pins 15 of the wafer lifting mechanism 14 can be vertically moved through the through holes 11b.

(1) The linear moving mechanism 19 is moved to the preset wafer mounting-and-dismounting position, and then stopped.

(2) The rotating mechanism 13 is rotated so that the through holes 11b of the wafer chuck 11 are at the preset wafer mounting-and-dismounting angle, and then stopped.

(3) The coupling member 21 is moved upward by expanding the air cylinder 22 so that the three pins 15 penetrate through the through holes 16 of the wafer chuck 11 and the top ends of the three pins 15 are projected by a preset level from the supporting surface 11a.

Figure 5:
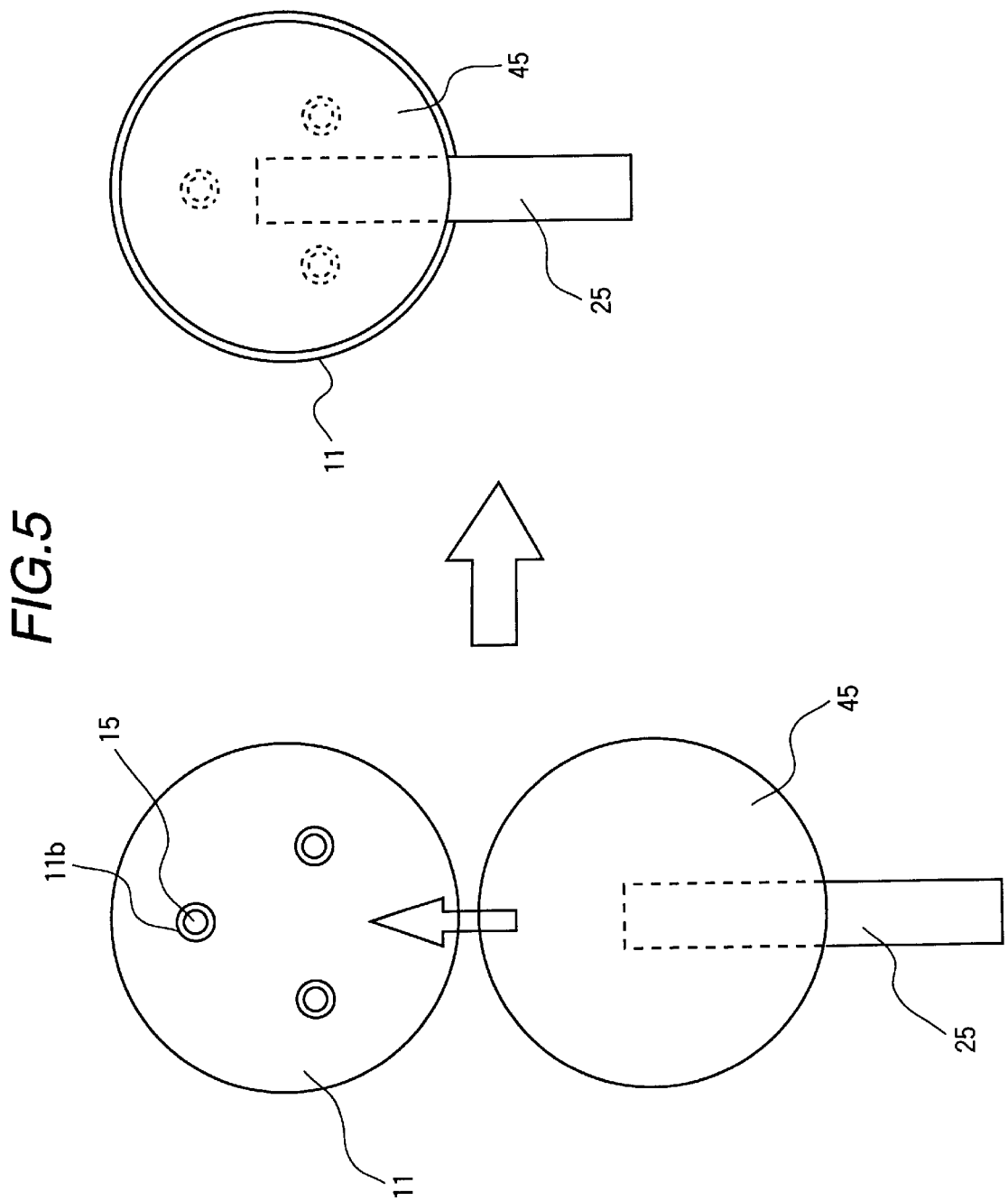
FIG. 5 is a view showing operation of arranging a silicon wafer on the wafer chuck.
Figure 6A:
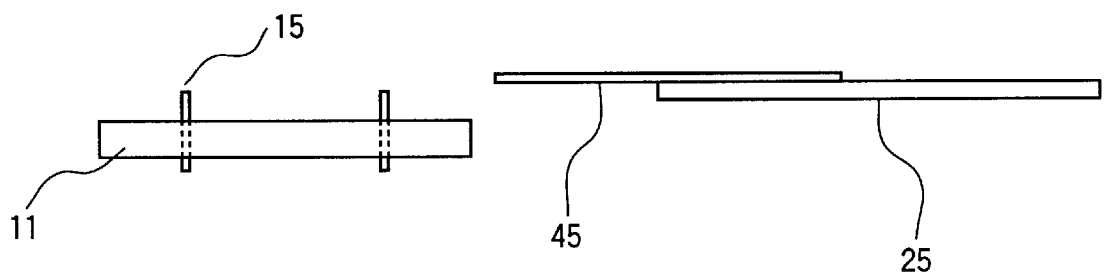
FIGS. 6A, 6B, 6C and 6D are side views showing the operation of arranging the silicon wafer on the wafer chuck.
Figure 6B:
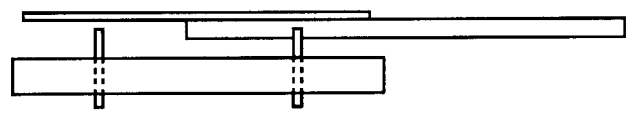
Figure 6C:
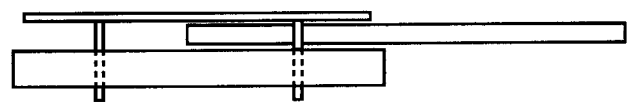
Figure 6D:

(4) The silicon wafer 45 held by the pair of tweezers 24 or supported by the transfer hand 25 is mounted onto the top ends of the three pins 15. Therein, the three pins 15 are arranged so as to stably hold the silicon wafer 45 and not contact with the transfer hand 25, as shown in FIG. 5. Although the silicon wafer is supported using the three pins in the apparatus of this embodiment, it is not limited to three pins but four pins or more may be acceptable. Two-point support may be also acceptable by using a member to be directly contacted with the silicon wafer.

(5) The evacuation control valve 20 is controlled so that the back surface of the silicon wafer 45 mounted on the top ends of the three pins 15 is adhered to the top ends of the three pins 15 by evacuating the sucking openings 15a of the top ends of the three pins 15.

(6) The silicon wafer 45 is released from supporting using the pair of wafer tweezers 24 or the transfer hand 25, and the pair of wafer tweezers or the transfer hand is drown back from the surface of the wafer chuck 11. Therein, a vacuum adhering mechanism is provided in the transfer hand 25, and is vacuum controlled so as to hold a silicon wafer when the silicon wafer is transferred.

(7) The coupling member 21 is moved downward by contracting the air cylinder 22. When the top ends of the three pins 15 are lowered to a preset level slightly higher than the supporting surface 11a of wafer chuck 11, the adhering of the silicon wafer 45 is stopped by stopping to evacuate the sucking openings 15a in the top ends of the pins 15 and, on the other hand, the sucking openings 11c of the supporting surface 11a of the wafer chuck 11 is started to be evacuated.

(8) By further contracting the air cylinder 22 to lower the three pins 15, the silicon wafer 45 is brought in contact with the supporting surface 11a of the wafer chuck 11, and adhered to the supporting surface 11a by a vacuum adhering force of the sucking openings 11c.

(9) The three pins 15 are moved and lowered to a preset level from the back surface of the wafer chuck 11 by further contracting the air cylinder 22 so as to not interfere rotating operation of the wafer chuck 11.

(10) Rotation and linear movement necessary for surface measurement of the silicon wafer 45 is performed using the rotating mechanism 13 and the linear moving mechanism 19.

FIGS. 6A, 6B, 6C and 6D are side views showing the procedure described above. As shown by FIGS. 6A, 6B, 6C and 6D, the silicon wafer 45 is transferred in a level higher than that of the pins 15 using the transfer hand 25 and moved downward after arriving above the wafer chuck 11, and the transfer hand 25 is drawn between the wafer chuck 11 and the silicon wafer 45 to a position sufficiently away from the silicon wafer 45. By moving the silicon wafer in such a manner, it is possible to suppress the interference between the silicon wafer 45 and the other members to minimum, and to transfer the silicon wafer without being damaged.

Next, description will be made below on the procedure of dismounting the silicon wafer 45 after completion of measurement from the wafer chuck 11.

(1) The linear moving mechanism 19 is moved to the preset wafer mounting-and-dismounting position, and then stopped.

(2) The rotating mechanism 13 is rotated so that the through holes 11b of the wafer chuck 11 are at the preset wafer mounting-and-dismounting angle, and then stopped.

(3) The coupling member 21 is moved upward by expanding the air cylinder 22 to move the three pins 15 upward.

(4) The sucking openings 11c of the supporting surface 11a of the wafer chuck 11 is stopped to be evacuated and, on the other hand, the sucking openings 15a in the top ends of the pins 15 is started to be evacuated.

(5) Further, the silicon wafer 45 is received onto the top ends of the three pins 15 from the supporting surface 11a of the wafer chuck 11 by moving the three pins 15.

(6) The three pins 15 are moved so that the top ends of the three pins 15 are projected by a preset level from the supporting surface 11a of the wafer chuck 11.

(7) The sucking openings 15a in the top ends of the three pins 15 is stopped to be evacuated.

(8) The silicon wafer 45 is dismounted by being held by the pair of tweezers 24 or being supported by the transfer hand 25.

Figure 4:
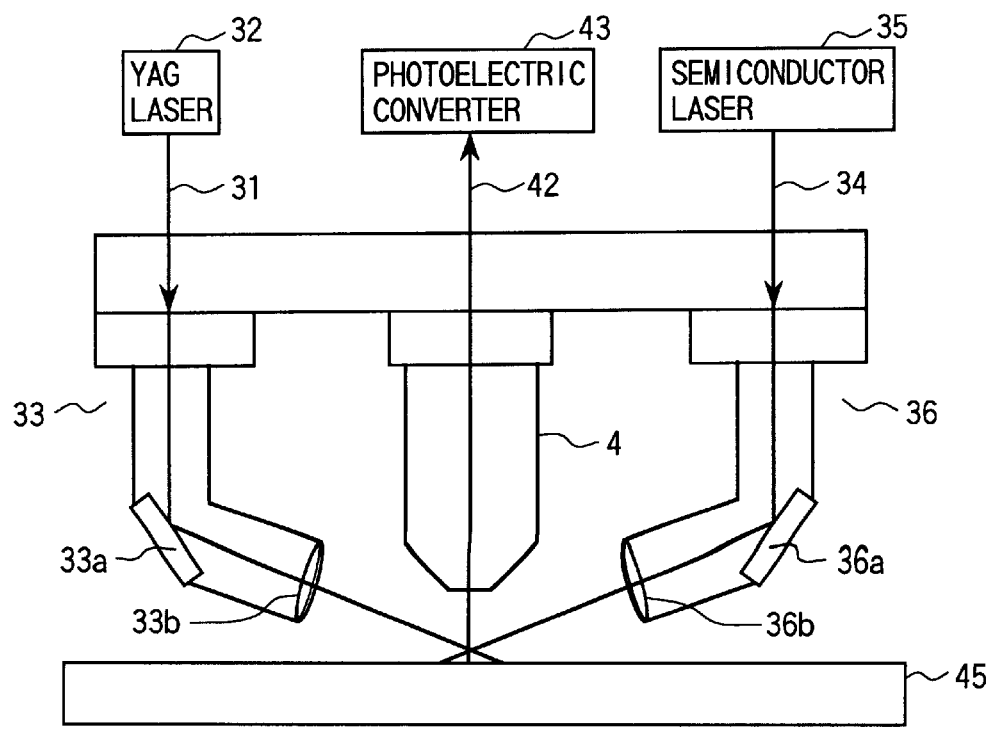
FIG. 4 is a side view showing an optical system in the wafer crystal defect measurement apparatus shown in FIG. 1.

FIG. 4 shows the above-mentioned light irradiating optical system 3 and the above-mentioned light receiving optical system 4 in a wafer crystal defect measurement apparatus in accordance with the present invention.

In the light irradiating optical system 3, a first irradiation light beam 31 is the light generated in a YAG laser 32 having 532 nm wavelength of which the polarization direction of the secondary harmonic light to the surface of the silicon wafer 45 is adjusted to p-polarization using a polarizer. In a first irradiating system 33, the first irradiation light beam 31 is reflected by a first reflecting mirror 33a, and condensed by a first condenser lens 33b, and then irradiated onto the surface of the silicon wafer 45 from a direction in which the optical axis of the incident light beam becomes the Brewster angle (75°) of silicon. Since the irradiation of p-polarization light beam at the Brewster angle is lower in the reflectivity on the silicon surface than that of s-polarization light beam, loss of irradiation light intensity to an internal defect can be reduced. This condition is preferable, but not always necessary.

A second light beam 34 is the light generated using a semiconductor laser 35 having 810 nm wavelength. In a second irradiating system 36, the second irradiation light beam 34 is reflected by a second reflecting mirror 36a, and condensed by a second condenser lens 36b, and then irradiated onto the surface of the silicon wafer 45 from a direction in which the optical axis of the incident light beam becomes the Brewster angle (75°) of silicon.

In regard to selection of wavelengths of the two irradiation light beams 31, 34 described above, two wavelengths having penetration depths to sample of the silicon wafer 45 different from each other by three times or more are selected. When the penetration depths are different from each other by three times or more, intensity attenuation of the long wavelength light becomes approximately 50% within a range of penetrable depth of the short wavelength light. Therefore, an error calculating a particle size of a scattering object from a scattered light signal of the long wavelength light through the Layleigh scattering theory can be estimated within 10%.

The light beams irradiated onto the silicon wafer 45 by the first and the second light irradiation systems 33, 36 are scattered by an internal defect of the silicon wafer 45. Among the scattered light, the forward scattered light cannot be turned back outside the wafer. Among the backward scattered light, scattered light having an angle lager than a critical angle (approximately 14.5 degrees) by the interface between silicon and air is totally reflected in the silicon wafer 45 and accordingly cannot be radiated outside the silicon wafer 45. Only the scattered light having an angle smaller than the critical angle passes through the interface between the silicon wafer 45 and air to be radiated outside the silicon wafer 45.

In the light receiving optical system 4, the scattered light radiated outside the silicon wafer 45 is trapped by an objective lens 41, and guided to a photoelectric converter 43 as a detected light beam 42. The photoelectric converter 43 converts an intensity of the detected light beam 42 into an electric signal.

In order to perform the measurement by irradiating the irradiation light beams 31, 34 on the surface of the silicon wafer over the whole area of the surface of the silicon wafer 45, a position irradiated by the irradiation light beams 31, 34 (a spot-shaped irradiated area) is moved on the surface of the silicon wafer 45 so as to trace a spiral path by supporting the silicon wafer 45 so that the silicon wafer 45 is rotated and the center is linearly moved using the wafer measuring state 1. When a scattering object passes through the irradiation area of the irradiation light beams 31, 34, a pulse of scattered light is generated. As the scattering object, there are a crystal defect such as an oxide precipitation ($SiO_2$ particle), a dislocation or the like contained inside the silicon wafer 45, and an extraneous particle attached on the wafer surface.

Measurement of the surface of the silicon wafer 45 and detection of a crystal defect are performed as follows.

A pulse of scattered light generated when a scattering object passes through the irradiation area of the irradiation light beams 31, 34 is condensed by the objective lens 41, and separated into scattered light of the first irradiation light beam 31 and scattered light of the second irradiation light beam 34 using a dichroic mirror, not shown, and the two kinds of scattered light are respectively converted into electric signals by respective photoelectric converting elements.

The microcomputer 5 receives the electric signals output from the respective photoelectric converting elements of the photoelectric converter 43, and the values (intensities) are displayed, recorded, stored and monitored. When the value exceeds a preset threshold value, it is judged that a defect (a scattering object to be detected) exists in that position. Rotation angle information θ and linear position information r obtained at that time from the stage control unit 2 are recorded or stored as the defect detection coordinates.

A method of accurately detecting a defect at the inside position near the surface of the sample or an extraneous particle attached onto the surface by irradiating two kinds of light beams having different wavelengths and measuring the scattered light as described above is disclosed in the specification and drawings of Japanese Patent Application Laid-Open No.10-26134. The apparatus in accordance with the present invention is suitable as a measurement apparatus for performing the detecting method disclosed in the specification and drawings of Japanese Patent Application Laid-Open No.10-26134.

According to the present invention, it is possible to prevent a sample from warping and bending by adhering almost all the area of the back surface of the sample onto a supporting surface of a sample chuck. Further, it is possible to make rotation of the sample chuck smooth and to make mounting and dismounting of the sample easy by arranging a sample lifting mechanism in a position separated from a rotating system of the sample chuck, the sample lifting mechanism lifting the sample off from the supporting surface by penetrating pins of the sample lifting mechanism through through holes of the sample chuck when the sample is mounted or dismounted on or from the supporting surface of the sample chuck at a sample mounting-and-dismounting position.

What is claimed is:

1. A surface measurement apparatus comprising a sample chuck for supporting a sample by adhering a back surface of the sample to a supporting surface; a moving mechanism for moving linearly and rotating the sample chuck; a base member for supporting the moving mechanism; a sample lifting mechanism for lifting the sample on the supporting surface of said sample chuck off from said supporting surface; and an optical measurement system for measuring the surface of the sample supported to said sample chuck to be rotated, wherein said supporting surface of the chuck comprises a flat surface for supporting the substantially whole periphery of an outer peripheral edge of the sample and through holes being formed in said flat surface and being passed through with plural lift pins provided on said sample lifting mechanism and said sample lifting mechanism is arranged in the side of said base member, said sample lifting mechanism extending said plural lift pins so as to lift the sample up from the supporting surface by penetrating said through holes with said plural lift pins when said sample chuck is stopped at a predetermined position where positions of said plural lift pins correspond to those of said through holes in a direction parallel to said supporting surface.

2. A surface measurement apparatus comprising a sample chuck for supporting a sample by adhering a back surface of the sample to a supporting surface; a rotating mechanism for rotating the sample chuck; a first base member for supporting the rotating mechanism; a second base member for linearly movably supporting the first base member; a sample lifting mechanism for lifting the sample on the supporting surface of said sample chuck off from said supporting surface; and an optical measurement system for measuring the surface of the sample supported to said sample chuck to be rotated, wherein said supporting surface of the chuck comprises a flat surface for supporting the substantially whole periphery of an outer peripheral edge of the sample and through holes being formed in said flat surface and being passed through with plural lift pins provided on said sample lifting mechanism, and said sample lifting mechanism is arranged in the side of said second base member, said sample lifting mechanism extending said plural lift pins so as to lift the sample up from the supporting surface by penetrating said through holes with said plural lift pins when said sample chuck is stopped at a predetermined position where positions of said plural lift pins correspond to those of said through holes in a direction parallel to said supporting surface.

3. A surface measurement apparatus according to claim 1, wherein said through hole is formed at a position keeping away from a position opposite to the outer peripheral edge of the sample to be mounted on and adhered to the supporting surface.

4. A surface measurement apparatus according to claim 1, wherein said sample lifting mechanism comprises a cylindrical pin vertically moved through said through hole.

5. A surface measurement apparatus according to claim 4, wherein said cylindrical pin in the sample lifting mechanism has a sucking opening for vacuum adhering at a top end of the cylindrical pin so as to vacuum adhere the back surface of the sample.

6. A surface measurement apparatus according to claim 5, wherein said sample chuck comprises a vacuum adhering system for vacuum adhering the sample onto the supporting surface, and said vacuum adhering system is released to atmospheric pressure and the cylindrical pin of the sample lifting mechanism is moved upward through the through hole while the sucking opening in the top end of the cylindrical pin is being evacuated when the sample supported on the support surface is lifted up from said supporting surface.

7. A surface measurement apparatus according to claim 4, wherein said sample lifting mechanism comprises a plurality of pins coupled with each other by a coupling member, said plurality of pins being vertically moved at a time by a single vertical drive mechanism.

8. A surface measurement apparatus according to claim 7, wherein said vertical drive mechanism comprises an air cylinder.

9. A surface measurement apparatus according to claim 1, wherein said optical measurement system comprises a light irradiating optical system for irradiating a light beam composed of two wavelengths of which penetration depth to the sample is different from each other by at least three times; and a light receiving optical system for converting an intensity of scattered light into an electric signal, the scattered light being scattered to any one of directions normal and oblique to the sample surface.

* * * * *